(12) United States Patent
Colling

(10) Patent No.: US 9,877,688 B1
(45) Date of Patent: Jan. 30, 2018

(54) X-RAY SHIELDING SYSTEM FOR USE WITH AN X-RAY PRODUCING GANTRY

(71) Applicant: Global Imaging Solutions Company, Livonia, MI (US)

(72) Inventor: Timothy P. Colling, Farmington Hills, MI (US)

(73) Assignee: GLOBAL IMAGING SOLUTIONS COMPANY, Livonia, MI (US)

( * ) Notice: Subject to any disclaimer, the term of this patent is extended or adjusted under 35 U.S.C. 154(b) by 0 days.

(21) Appl. No.: 15/617,509

(22) Filed: Jun. 8, 2017

Related U.S. Application Data

(63) Continuation-in-part of application No. 15/427,414, filed on Feb. 8, 2017.

(51) Int. Cl.
*A61B 6/00* (2006.01)
*A61B 6/10* (2006.01)
*G21F 3/00* (2006.01)

(52) U.S. Cl.
CPC ................ *A61B 6/107* (2013.01); *G21F 3/00* (2013.01)

(58) Field of Classification Search
CPC .......... A61B 6/107; A61B 6/0407; G21F 3/00
USPC ...................... 250/505.1, 515.1, 517.1, 519.1
See application file for complete search history.

(56) References Cited

U.S. PATENT DOCUMENTS

| | | | |
|---|---|---|---|
| 5,099,135 A | | 3/1992 | Gemmill |
| 5,417,225 A | * | 5/1995 | Rubenstein ............ A61B 90/04 |
| | | | 128/849 |
| 5,981,964 A | * | 11/1999 | McAuley ............... A61B 6/107 |
| | | | 250/515.1 |
| 6,448,571 B1 | | 9/2002 | Goldstein |
| 6,653,648 B2 | | 11/2003 | Goldstein |
| 6,703,632 B1 | | 3/2004 | Macklis et al. |
| 9,177,681 B2 | | 11/2015 | Morris |
| 9,451,922 B2 | | 9/2016 | Buchmeyer |
| 2012/0148335 A1 | | 6/2012 | Nourry et al. |

FOREIGN PATENT DOCUMENTS

| | | |
|---|---|---|
| CN | 201127616 | 10/2008 |
| DE | 2614202 | 10/1977 |

OTHER PUBLICATIONS

International Search Report for PCT/US2017/030509, Issued by the U.S. Patent and Trademark Office, dated Aug. 17, 2017.

\* cited by examiner

*Primary Examiner* — Michael Maskell
(74) *Attorney, Agent, or Firm* — Brooks Kushman P.C.

(57) ABSTRACT

Disclosed is a shielding system for customized shielding of a patient or an operator from X-rays generated by a gantry. The shielding system is mounted on the gantry. The system has a rail that is arcuately movable in relation to gantry-mounted foundational blocks with apertures that receive movable rails from which protective curtains are suspended.

7 Claims, 2 Drawing Sheets

X-RAY SHIELDING SYSTEM FOR USE WITH AN X-RAY PRODUCING GANTRY

CROSS-REFERENCE TO RELATED APPLICATIONS

This application claims the benefit of and is a continuation-in-part of U.S. Ser. No. 15/427,414 which was filed on Feb. 8, 2017, the disclosure of which is incorporated herein in its entirety.

TECHNICAL FIELD

This disclosure includes a customizable x-ray shielding system for primary use with an X-ray producing gantry.

BACKGROUND

As used herein, the term "gantry" includes the 'donut' shaped part of a CT scanner that houses the components necessary to produce and detect x-rays to create a CT image. Typically, the x-ray tube and detectors are positioned opposite each other and rotate around the gantry aperture.

Among the art considered in preparing this patent application are these references: U.S. Pat. Nos. 5,099,135; 5,417,225; 6,448,571; and 6,653,648.

SUMMARY

Disclosed is a shielding system for customized protection from X-rays. The shielding system is mounted on an x-ray producing gantry. The gantry, if desired, can be tilted so that it may lie in a plane that is about, for example, plus or minus 45 degrees from a vertical plane.

In use over the various orientations of such machines there is a need to isolate the technician or physician from X-radiation. To do this, shielding devices such as lead or other radio-opaque curtains are often used. But such curtains need to be suspended from a movable rail so that their placement is predictable, yet adjustable regardless of machine orientation.

One way to achieve the goal of reliably supporting such shielding devices is to suspend them from a rail that is mounted in a foundational block which is affixed preferably to an upright or other face of the movable gantry. Optionally the block can be secured to a gantry-mounted track that enables the block's position to be further adjusted. If desired, multiple foundational blocks may be affixed to the gantry.

Facing an upright, usually vertical plane of the gantry is a back surface (A) of each foundational block. A post-receiving aperture extends between the top surface (C) and an opposing bottom surface (D). Each aperture is configured to receive a proximal end region of an arcuately movable rail from which, for example, a radio-opaque curtain can be suspended if desired under the influence of gravity in a vertical plane. One or more detents are defined by the top surface (C). At least some of the detents are configured to be in registration with one or more lugs that extend radially from a proximal end region of the bracket. Upon registration, there is little or no twisting movement of the rail in relation to the foundational block.

Extending from the proximal section of the rail is a distal section. In use, a rail can be turned within an associated aperture. Regardless of gantry orientation, one or more radio-opaque curtains can be suspended from a given rail in a desired position from the distal section by twisting the proximal end region, rotating it in relation to the associated aperture and then seating one or more lugs in a suitable detent.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Disclosed is a shielding system 10 for use in alternative configurations as user-selected, customized shielding from X-rays. The shielding system 10 is mounted on a base such as a gantry 12. In use, the usually near-vertical plane of the gantry 12 can be tilted if desired through an angular range of about 45 degrees from a vertical plane.

Figure 1:
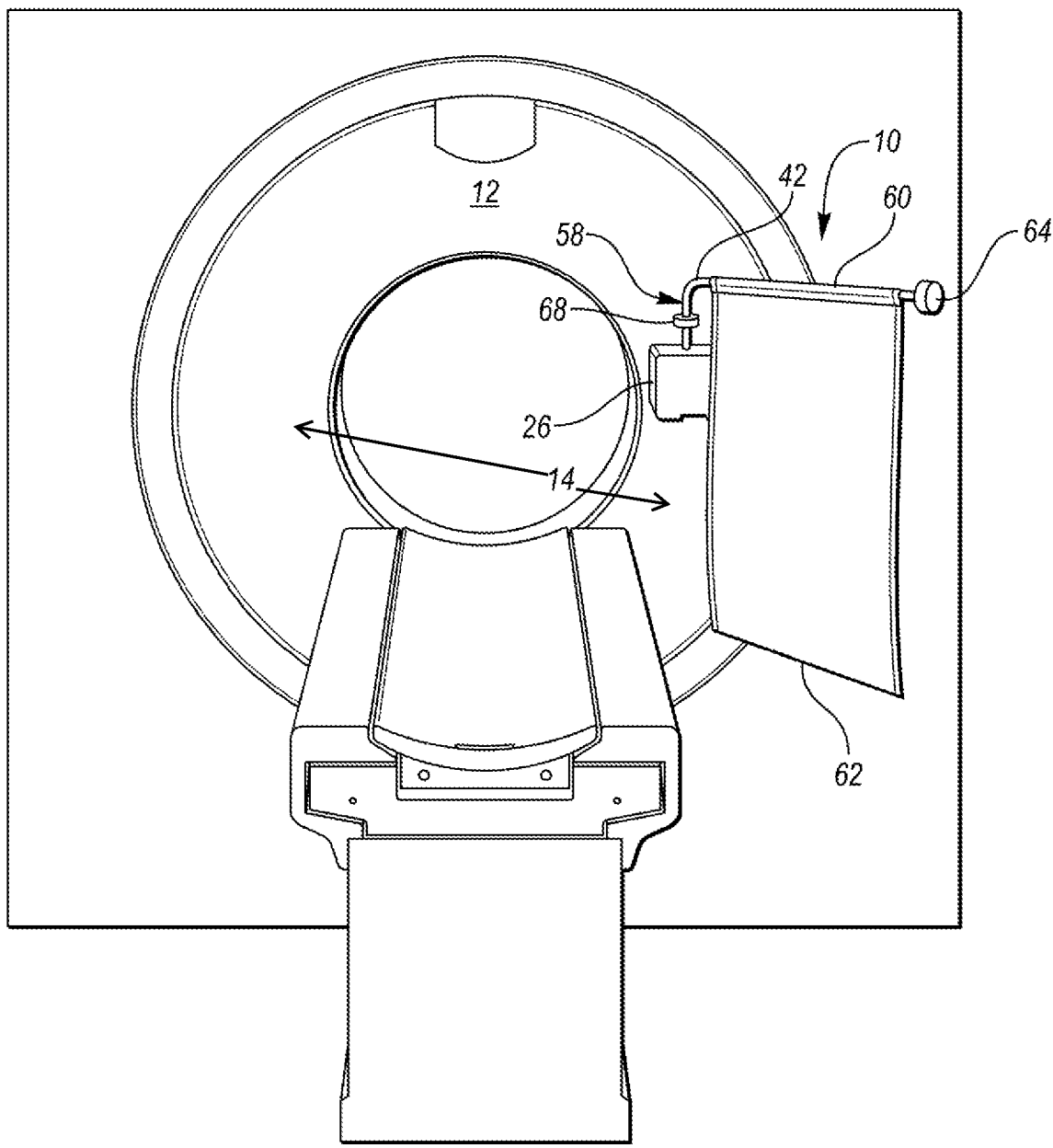
FIG. 1 is a quartering perspective view of a typical environment in which a shielding system is deployed, including a rail from which a lead curtain is suspended.

In the shielding system 10 associated with a given gantry, there are one or more foundational blocks 26 (see, e.g. FIG. 1).

Figure 2:
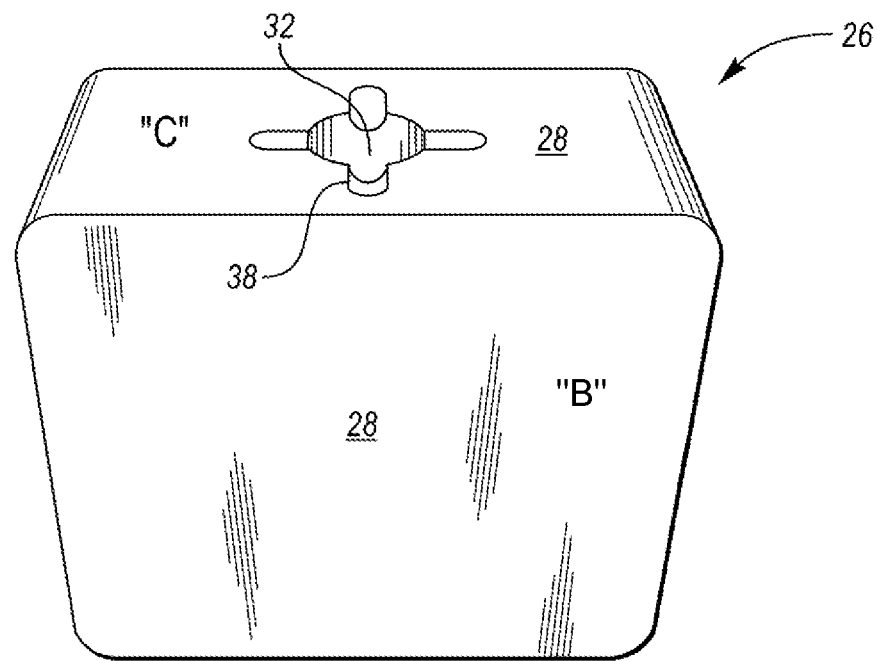
FIG. 2 depicts a representative top surface (C) with detents that receive lugs extending from a proximal end region of the rail and front surface (B) of a foundational block that form a part of the shielding system.
Figure 3:
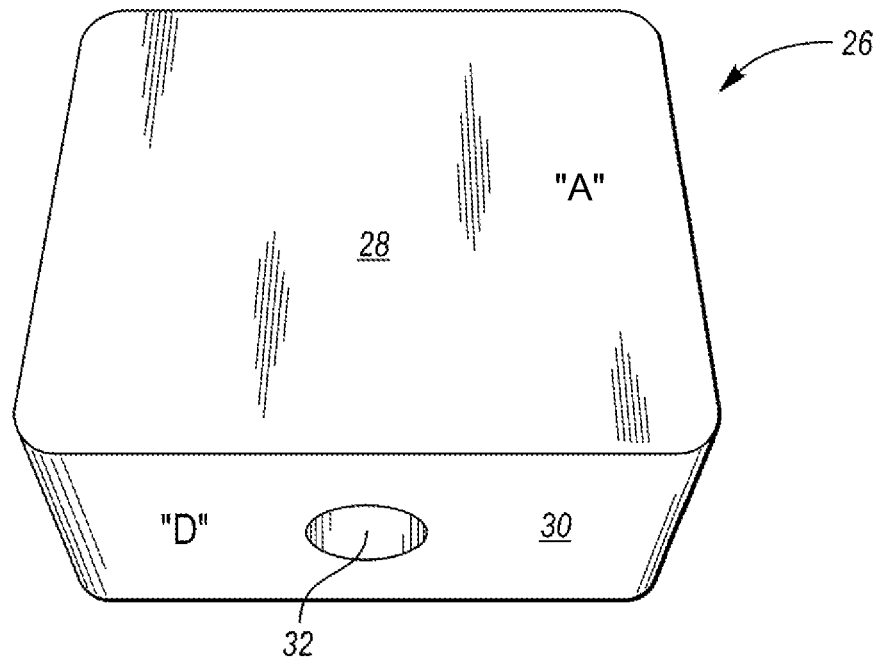
FIG. 3 depicts a representative bottom surface (D) and back gantry-facing surface (A) of the foundational block.

Facing the block-mounting mounting surface 14 of the gantry 12 is a back surface (A) 28 of the foundational block (FIG. 3). A post-receiving aperture 32 extends between the top surface (C) 28 (FIG. 2) and an opposing bottom surface (D) 30 (FIG. 3). One or more detents 38 are defined within the top surface (C). Each detent 38 is configured to be in registration with a lug or pin that extends generally radially from the rail 42. Upon registration of the rail 42 within an associated detent 38, there is little or no twisting movement of the rail 42 in relation to the foundational block 26.

One or more apertures 32 extend between the bottom surface (D) 28 and the opposing top surface (C) 30. Each major aperture is configured to receive a rail 42.

Each rail 42 has a proximal section 58 (FIG. 1) that is received by a major aperture 32 of a foundational block 26. Extending from the proximal section 58 is a distal section 60. It will be appreciated that the distal section 60 need not be orthogonal with the proximal section 58. Other angular relationships between about 30 and 90 degrees may be desirable, depending on the installation. Regardless of gantry orientation, one or more radio-opaque curtains 62 can be hung from the distal section 60 to allow flexibility in adapting to operator and patient examination requirements. It will be appreciated that the curtains 62 are preferably formed from an x-ray absorbing material. Such curtains 62 may for example be 20" long×26" wide. But the curtains 62 can be of any length and width. Further, the curtains 62 may have any desired x-ray attenuation characteristics.

In one embodiment, there is a knob 64 that is received at an end of the distal section 60 of the rail 42 for constraining lateral movement of the one or more radio-opaque curtains 62 along the distal section 60 of the rail 42.

Preferably the apertures 32 terminate at the opposing top surface (C) 28 (FIG. 2) and slots 38 extend radially from the apertures 32. The slots 32 are configured to engage lugs 68 that extend radially from the proximal section 58 of the rail 42 to preclude a twisting motion of the rail 42 when seated within an associated aperture 32. This feature influences rail positioning regardless of gantry orientation.

In most uses, a rail 42 can be twisted within an associated major aperture 32 so that the distal section 60 of the rail 42 can be made to extend substantially horizontally regardless of gantry orientation.

Optionally, the rail position is secured by engaging a lug 68 within a slot 38. It will be appreciated that the distal section 60 of the rail 42 may be arcuately positioned so that the distal section 60 extends horizontally. Optionally, if desired, the distal section 60 may lie in parallel with a face of the gantry.

In some cases, each gantry has one or two foundational blocks 26 for optimized shielding of the patient and operator from radiation. Each block 26 supports a rail 42. Preferably there are up to four blocks 26 per gantry. Placement of the block 26 is not restricted to a front face of the gantry. For example, one pair of blocks 26 may be positioned behind another pair of blocks so that one curtain 62 may be positioned partially behind another curtain.

To secure a foundational block 26 in relation to the gantry, means for securement are provided. Such securement means include, for example, a threaded bolt, a screw, a rivet, cement or a glue.

In some cases, the gantry orientation lies between plus and minus 45 degrees from a vertical plane.

Although the foundation blocks 26 are depicted as generally brick-shaped, it will be appreciated that such blocks may be shaped in various geometries and sizes, and have non-parallel faces that may or may not be planar.

TABLE OF REFERENCE NUMERALS

10 shielding system
12 gantry
26 foundational blocks
28 back (gantry-facing) surface (A)
30 bottom surface (D)
32 post-receiving aperture
38 detent
42 rail
58 proximal section of rail
60 distal section
62 radio-opaque curtain
64 knob
68 lugs While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An x-ray shielding system for customized shielding from x-rays generated by a gantry, the shielding system comprising:
   one or more foundational blocks, each block having
   a bottom surface and an opposing top surface;
   a rail-receiving aperture that extends at least partially between the bottom surface and the opposing top surface;
   a detent defined by the top surface, the detent being configured to be in registration with a lug that extends radially from the rail so that upon registration, there is little or no movement of the rail in relation to the foundational block;
   the rail having a proximal section that is received by the rail-receiving aperture and a distal section that extends from the proximal section so that one or more radio-opaque curtains can be suspended from the distal section.

2. The shielding system of claim 1, further including:
   a knob that is received at an end of the distal section of the rail for constraining lateral movement of the one or more radio-opaque curtains along the distal section of the rail.

3. The shielding system of claim 1, wherein the rail-receiving aperture terminates at the top surface and the detents extend radially from the post-receiving aperture, the detents being configured to engage lugs that extend radially from the proximal section of the rail to preclude a twisting motion of the rail within an associated aperture when the proximal section is seated, thereby influencing rail positioning regardless of gantry orientation.

4. The shielding system of claim 1, wherein one rail orientation is a generally horizontal orientation.

5. The shielding system of claim 1, wherein one rail orientation is a forward orientation.

6. The shielding system of claim 1, wherein the rail can be twisted within the aperture so that the distal section of the rail extends horizontally regardless of gantry orientation.

7. The shielding system of claim 1, wherein there are two foundational blocks, each supporting one or more rails, each rail having a distal section extending horizontally, and the other rail having a distal section that lies in another orientation.

* * * * *